United States Patent
Walsh

[11] Patent Number: 6,099,162
[45] Date of Patent: Aug. 8, 2000

[54] RESIN CURE MONITOR

[75] Inventor: Thomas J. Walsh, Houston, Tex.

[73] Assignee: Hydril Company, Houston, Tex.

[21] Appl. No.: 08/957,254

[22] Filed: Oct. 24, 1997

[51] Int. Cl.[7] ............ G01K 17/00; G01K 17/20; G01N 3/26
[52] U.S. Cl. ............ 374/30; 374/32; 374/53; 250/341.1
[58] Field of Search ............ 374/10, 11, 29, 374/30, 32, 33, 39, 40, 43, 53; 250/338.1, 339.03, 340, 341.1, 341.2

[56] References Cited

U.S. PATENT DOCUMENTS

| | | | |
|---|---|---|---|
| 4,216,253 | 8/1980 | Bonnebat et al. | 428/35 |
| 4,325,903 | 4/1982 | Wissbrun et al. | 264/176 |
| 4,363,968 | 12/1982 | McGowan et al. | |
| 4,551,807 | 11/1985 | Hsich et al. | |
| 4,574,066 | 3/1986 | Gibbon et al. | 264/85 |
| 4,582,520 | 4/1986 | Sturm | |
| 4,591,475 | 5/1986 | Tomka et al. | |
| 4,609,628 | 9/1986 | Aschenbeck | |
| 4,764,320 | 8/1988 | Chau et al. | 264/41 |
| 4,773,021 | 9/1988 | Harris et al. | |
| 4,819,177 | 4/1989 | Jurgensen | |
| 4,824,619 | 4/1989 | Okada et al. | 264/40.1 |
| 4,902,460 | 2/1990 | Yagi et al. | 264/83 |
| 4,996,291 | 2/1991 | Yoshinaka et al. | 528/272 |
| 5,001,068 | 3/1991 | Golombek | |
| 5,009,102 | 4/1991 | Afromowitz | |
| 5,009,104 | 4/1991 | Johnson | |
| 5,051,222 | 9/1991 | Marten et al. | 264/143 |
| 5,100,605 | 3/1992 | Bartlet et al. | 264/143 |
| 5,142,151 | 8/1992 | Varnell et al. | |
| 5,158,720 | 10/1992 | Levy | |
| 5,158,858 | 10/1992 | Lawton et al. | 430/269 |
| 5,211,477 | 5/1993 | Li | |
| 5,224,775 | 7/1993 | Reading et al. | |
| 5,248,199 | 9/1993 | Reading | |
| 5,264,534 | 11/1993 | Kovar et al. | 528/125 |
| 5,276,085 | 1/1994 | Kasowski et al. | 524/606 |
| 5,288,147 | 2/1994 | Schaefer et al. | |
| 5,360,672 | 11/1994 | Saito et al. | 428/480 |
| 5,366,812 | 11/1994 | Takahashi et al. | 428/523 |
| 5,374,708 | 12/1994 | Tamai et al. | 528/353 |
| 5,436,565 | 7/1995 | Gammell | |
| 5,439,291 | 8/1995 | Reading | |
| 5,549,943 | 8/1996 | Vicik | 428/34.8 |
| 5,618,480 | 4/1997 | Van Den Heuvel et al. | 264/103 |
| 5,624,187 | 4/1997 | Reading | |

FOREIGN PATENT DOCUMENTS

| | | |
|---|---|---|
| 4040352 A1 | 7/1992 | Germany . |
| 2208552 | 4/1989 | United Kingdom . |
| WO 97/11357 | 3/1997 | WIPO . |

OTHER PUBLICATIONS

Internet address funnelweb.utcc.utk.edu/~athas/reports/407/407–1a.html.
Internet address funnelweb.utcc.utk.edu/~athas/reports/407/407–1b.html.
Internet address funnelweb.utcc.utk.edu/~athas/reports/407/407–1c.html.
Internet address funnelweb.utcc.utk.edu/~athas/reports/407/407–1d.html.
Internet address funnelweb.utcc.utk.edu/~athas/reports/407/407–1e.html.
Internet address funnelweb.utcc.utk.edu/~athas/reports/407/407–1f.html.
Internet address www.perkin–elmer.com/thermal/ta13a.html.
Internet address www.tainst.com/dsc.htm.
Internet address funnelweb.utcc.utk.edu/~athas/reports/report95/rep95md.

*Primary Examiner*—Vit Miska
*Attorney, Agent, or Firm*—Rosenthal & Osha L.L.P.

[57] ABSTRACT

The curing of a resin in a continuous manufacturing process is monitored by a sensor which measures the surface thermal energy of the resin. The surface thermal energy is measured without physically touching the resin. The surface thermal energy measurements are processed and sent to an automatic controller. The controller adjusts either the speed of the resin or the heat applied to the resin or both in order to optimize the curing process.

30 Claims, 4 Drawing Sheets

RESIN CURE MONITOR

STATEMENT AS TO FEDERALLY SPONSORED RESEARCH

The U.S. Government has a paid-up license in this invention and the right in limited circumstances to require the patent owner to license others on reasonable terms as provided for by the terms of Award # 70NANB5H1053 awarded by the Department of Commerce, National Institute of Standards and Technology—Advanced Technology Program.

BACKGROUND OF THE INVENTION

Resins have widespread use in today's manufacturing processes. When a material that incorporates a resin is manufactured, obtaining a desired degree of cure is a primary consideration. A completed cure will allow optimization of desired properties of the material, including hardness and strength. However, uncertainties regarding the characteristics of the materials involved and the thermodynamics of the manufacturing process complicates the curing process. Too long of a cure period can have an adverse impact on properties of the material and unnecessarily increase cost. Too short a period is also undesirable. The need for a control process is therefore manifest. An ideal cure control system should control the process regardless of the composition of the material.

A successful cure of polymeric materials, such as an epoxy resin, is accomplished when cross-linking occurs between the polymers. In most curable materials, this process involves reactions that absorb heat (endothermic) and that radiate heat (exothermic). A full cure is achieved when the amount of energy being applied to a material matches the amount of heat being radiated by that material. This equilibrium indicates that the endothermic and exothermic reactions have reached a steady state and the curing process is complete.

The curing requirements of a particular material can be represented by a cure profile. However, the profile will vary among different materials and even among batches of the same material. Most composite manufacturers attempt to create a cure profile to process their composites at optimum efficiency. One method of creating a cure profile involves destructive thermal analysis of a sample of a partially cured material. The sample is removed from the material during the cure process and is analyzed using techniques such as digital scanning calorimetry (DSC), thermomechanical analysis (TMA), thermogravimetric analysis (TGA), dynamic mechanical analysis (DMA), or any other techniques well known it the art. These techniques involve multiple experiments and destruction of, or at a minimum contact with, the sample.

The use of destructive thermal analysis is ideally suited to a batch production process. A batch process involves the production of a specified quantity of material at one time. Sampling of the material for destructive thermal analysis is relatively simple because the curing procedure can be interrupted without an undue reduction in production. In contrast, a continuous production process involves continually producing material in a constant stream. In a continuous process, sampling is not feasible without halting the entire production stream.

SUMMARY OF THE INVENTION

In some aspects, the invention relates to an apparatus for monitoring curing of a member, including a resin which comprises an energy source arranged to apply energy to the member and a sensor which monitors the curing by detecting the surface thermal energy of the member.

In an alternative embodiment, an invention relates to an apparatus for verifying complete curing of a resin in a continuous manufacturing process which comprises a plurality of heaters arranged to apply heat to the resin, a plurality of sensors which detect the thermal surface energy of the resin without contact with the resin, an output device which processes the thermal surface energy from the sensors, and an automatic controller which adjusts either the speed of the resin or the energy applied to the resin.

In an alternative embodiment, the invention relates an apparatus for monitoring curing of a member which comprises a means for applying energy to the member, a means for detecting the thermal surface energy of the member, a means for processing the thermal surface energy of the member, and a means for automatically controlling the curing parameters based on the surface thermal energy.

In an alternative embodiment, the invention relates to a method for monitoring curing of a resin which comprises applying heat to a resin, monitoring the surface thermal energy of the resin without contact with the resin, processing the surface thermal energy of the resin, determining if the resin has reached a complete cure, and adjusting either duration or intensity of the energy application or both.

DESCRIPTION OF THE PREFERRED EMBODIMENTS

The preferred embodiments of the invention are described with reference to the accompanying figures. Like references in different figures are shown with the same numeral.

In accordance with the invention, an apparatus and method are disclosed for creating a cure profile of a material by measuring the surface thermal energy. This energy is generated by the exothermic reaction of the curing process. One method of detecting the surface thermal energy involves intimate contact with the material. The contact involves embedding a sensor permanently in the body of the material. Another option is doping the material with a substance that signals the degree of cure. However, the preferred method for measuring the surface thermal energy detects the energy without physical contact with the material. This approach lends itself to use as part of a continuous curing process as opposed to a batch curing process. Because the sensors do not interfere with the material being cured, a reduction in overall cure times and an increase in production rates is possible.

Figure 1:
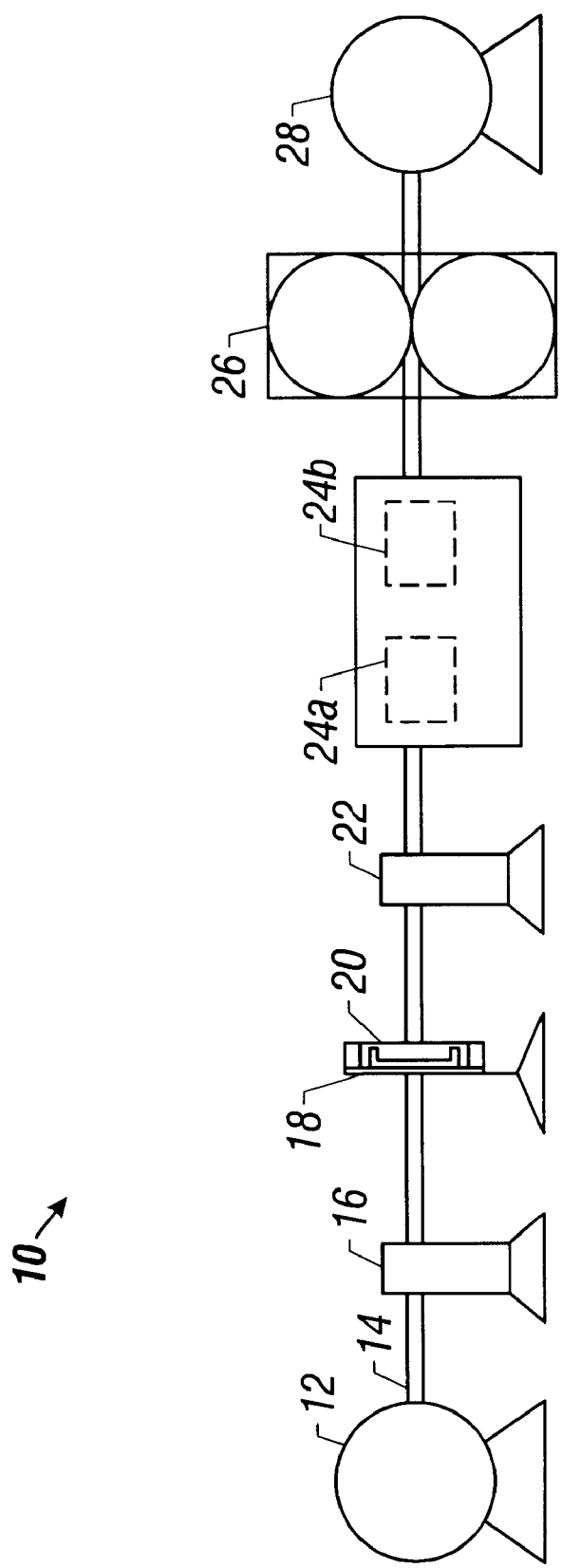
FIG. 1 is an example of manufacturing line for a composite pipe.

FIG. 1 shows an example of a manufacturing operation for composite pipe employing a continuous curing process. The composite pipe manufacturing line 10 begins with a liner coil 12. The liner 14 will serve as the foundation for the finished pipe. The liner may be a thermoplastic, thin steel, or any other suitable material known in the art. The liner 14 is uncoiled and pulled through an adhesive bath 16 in preparation for application of fiber windings 20. The fiber windings 20 are applied by a winder 18 which rotates about the liner 14. The windings may also be braided or laid axially, or in accordance with any other known method. The fiber, also known as tows, may be a carbon fiber, fiberglass, or any other suitable material known in the art. Additionally, any combination of these fibers may be used. The next station is a resin bath 22 which applies resin to the liner 14 and fiber windings 20. The resin may be an epoxy, vinyl ester, or polyester resin, or any other type of conventional resin. The composite is then cured in passing through multiple curing units (Two curing units 24a and 24b we show for instruction purposes). The cured composite pipe then passes through a pulling tractor 26 and is spooled out a finished pipe coil 25. Although only one adhesion bath 16, one winder 18, one resin bath 22, and two curing units 24a and 24b are shown in FIG. 1, this is for purposes of instruction only. In an actual production line, a plurality of each of these elements may be used depending upon the type of composite being manufactured.

Figure 2:
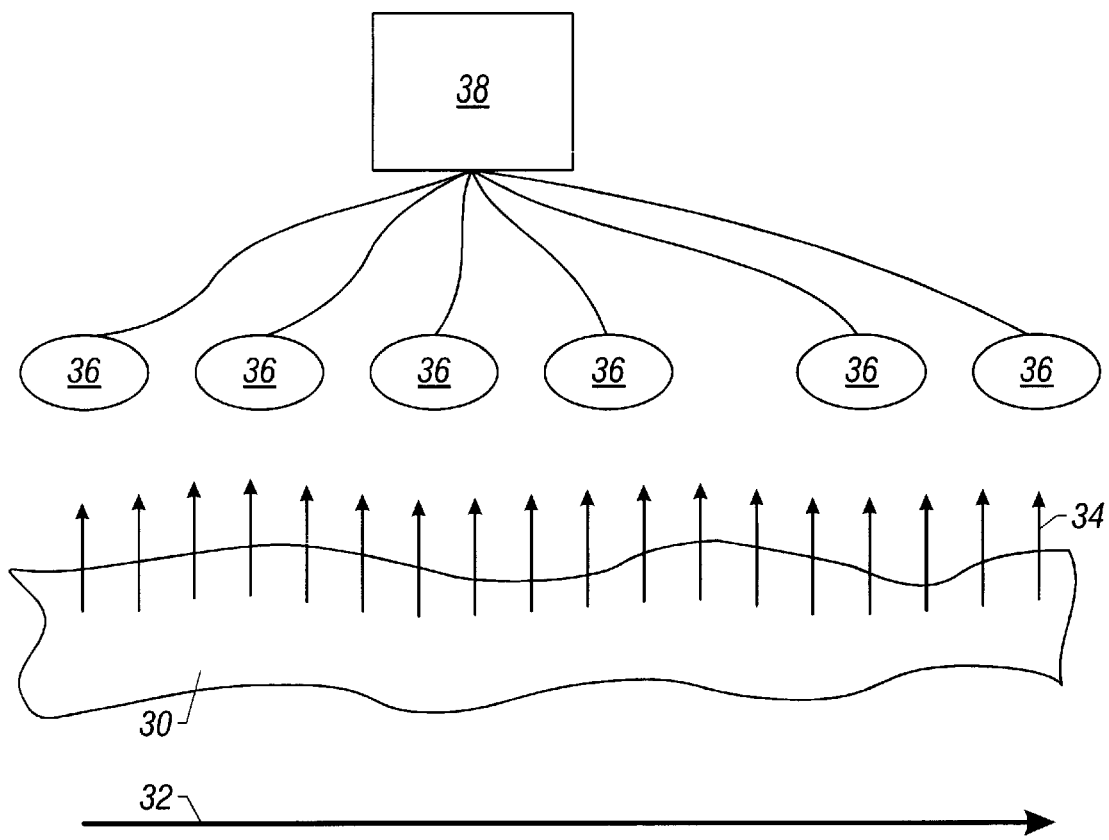
FIG. 2 illustrates a cure monitor in accordance with one embodiment of the invention for use with a continuous manufacturing operation.

A continuous manufacturing process is greatly benefitted by a continuous curing process because it does not interrupt production. However, accurate monitoring of a continuous curing process was unavailable in the prior art. FIG. 2 shows a continuous cure monitor in accordance with an embodiment of the invention wherein the member 30 being cured, which may be a composite, is in motion in the direction 32 adjacent to multiple sensors 36. The sensors 36 measure the surface thermal energy 34 radiated by the member 30. The results from the sensors 36 are stored in a processing device 38. These results are used to generate a cure profile for the element 30, from which the degree of cure can be determined.

Figure 3:
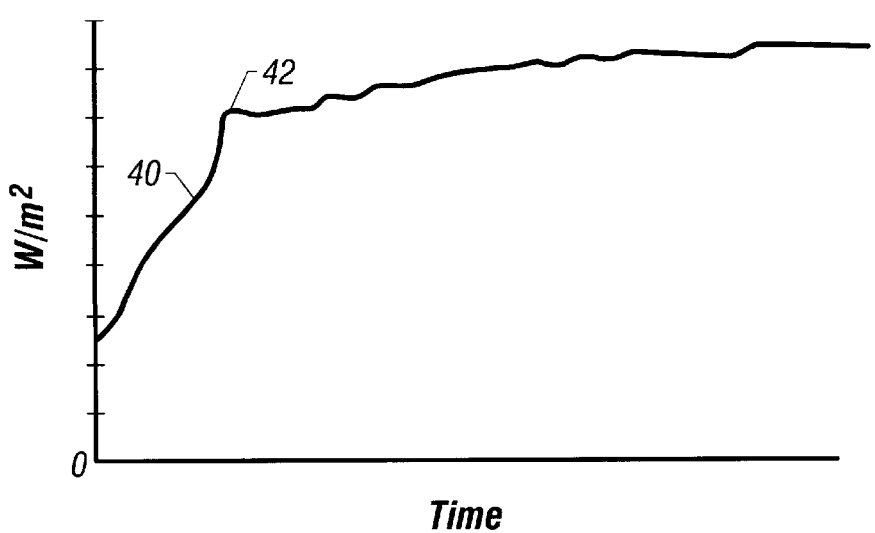
FIG. 3 is an example graph of a cure profile.

An exemplary graph of a cure profile is shown in FIG. 3. The x-axis represents the length of time that the material has been in the cure cycle. The y-axis represents the surface thermal energy radiated by the material, expressed in Watts/meter$^2$. However, any other suitable units of measure could be used. The spike 40 near the beginning of the curve indicates a rapid thermal reaction. Thermal equilibrium is achieved at the cure completion point 42 as indicated by the curve reaching a plateau. At this point, the cure process of the material is complete. Thus, complete curing can be verified in a continuous process by ensuring that the cure completion point 42 is reached as the member passes through the cure process.

Figure 4:
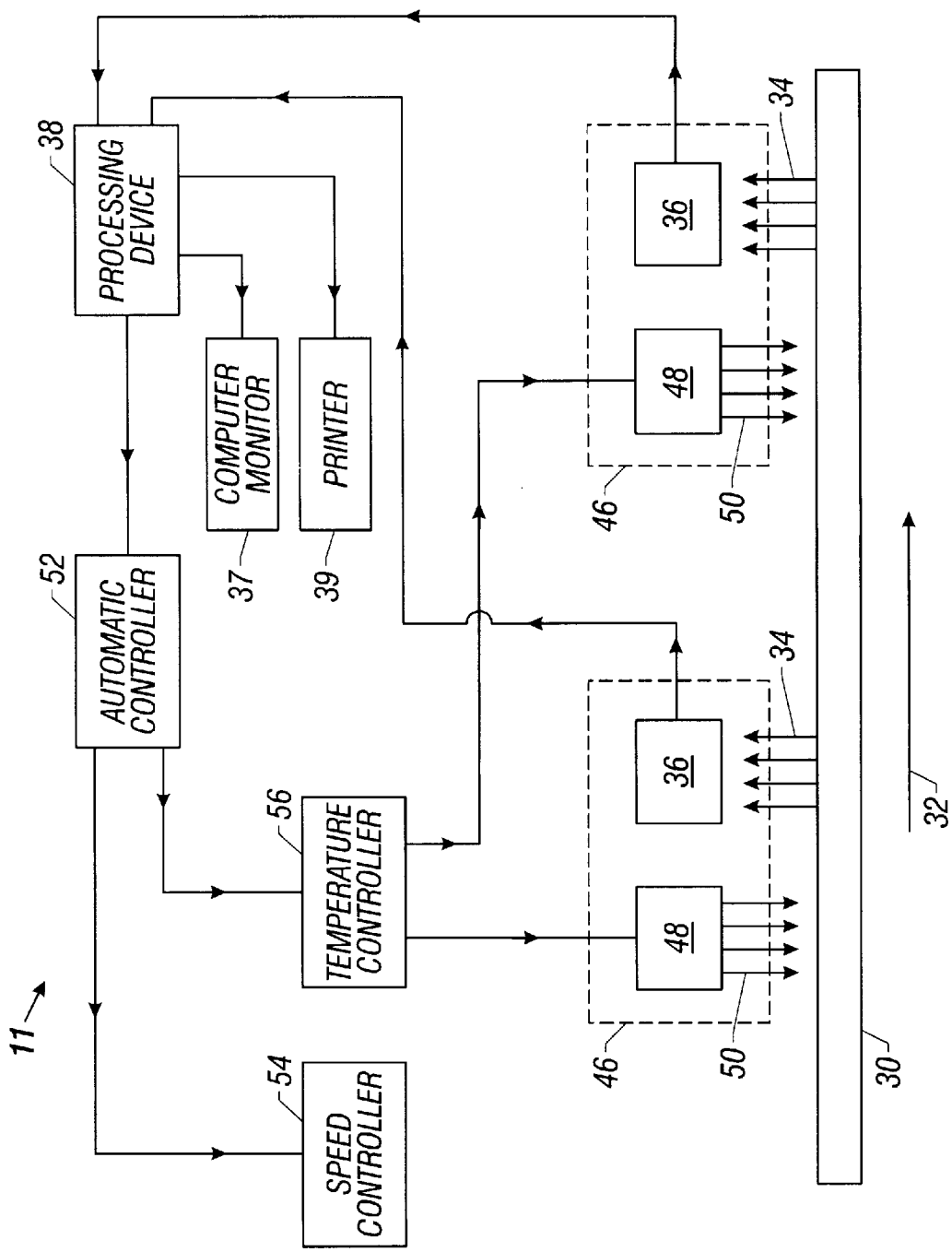
FIG. 4 is a schematic of a continuous curing process in accordance with the embodiment of FIG. 2.

FIG. 4 shows a detailed view of a continuous curing process. Member 30 to be cured is in motion in direction 32 adjacent to multiple curing units 46. The member 30 which is being cured may be a composite of several materials such as a liner, different types of fibers, an overwrap, and polymeric materials such as resins. Any material or composites of materials which require curing may use this process.

A curing unit 46 includes a cure energy generator 48 and a sensor 36. While two curing units 46 are shown, any number could be used according to the specific circumstances. Additionally, any number of individual cure energy generators 48 or individual sensors 36 could be used independent of any curing units 46. In a preferred embodiment, seven independent curing units are used for a production rate of 1000 lb/hr of a carbon/epoxy composite.

The cure energy generator 48 generates the cure energy 50 that is applied to the element 30. These generators are located at various locations along the curing area. The cure energy 50 may be radiant heat, hot oil, microwaves, or any other appropriate type of energy that is known in the art. The cure energy generator 48 may be a heater, oven, lamp or any other device that is capable of generating the type of cure energy 50 that is applied. The surface thermal energy 34 of the element 30 is detected by the sensors 36 which are located at various locations along the curing area. In a preferred embodiment, the sensors are an OMEGA Unit Model # 05910C.

The sensors 36 send the surface thermal energy data to a processing device 38. The processing device 38 processes the data for possible output to a computer monitor 37, a printer 39 or an automatic controller 52. The processing device 38 may be any device that is capable of recording or storing data such as a computer or a data plotter. Any stored data may be used to generate a cure profile. The processing device 38 plots the amount of surface thermal energy 34 against the length of time of the cure or the length of the cure area. Preferably, this data can be displayed as a graph in a format such as a computer monitor 37 or a, printer 39. The data can be compared to an existing database of cure profiles to determine the degree of cure.

The processing device 38 outputs its data to an automatic controller 52. The automatic controller 52 can then adjust cure parameters, including for example speed and energy, based on this output. The cure parameters such as duration and intensity are controlled by either the speed controller 54 for the element 30 or the temperature controller 56 for the cure energy generator 48. The automatic 52 controller is used to optimize the production rate by minimizing the cure time while still ensuring that a cure is completed. In an alternative embodiment, manual control may be used. In this embodiment, an operator monitors the cure profile generated by the processing device 38. The operator determines the degree of cure and makes any necessary adjustments to the speed controller 54 and/or the temperature controller 56.

Figure 5:
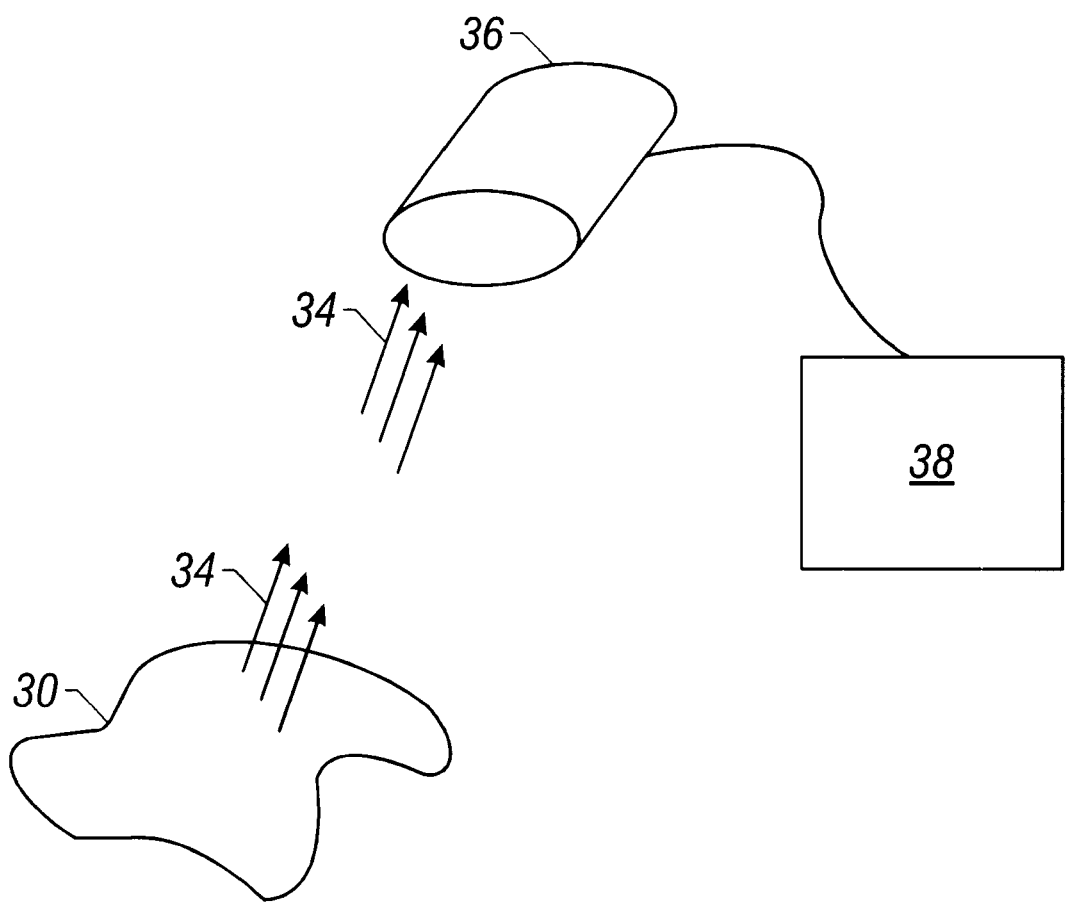
FIG. 5 is a batch cure monitor in accordance with one embodiment of the invention for use with a batch manufacturing operation.

As explained above, it is preferable that the sensors 36 do not contact the member 30. This allows the curing to be a continuous process because the movement 32 of the element 30 is uninterrupted throughout the production run. However, the cure monitoring of the invention may also be used advantageously as part of a batch process. As shown in FIG. 5, a batch cure monitoring involves a sample of an element 30 whose surface thermal energy 34 is detected by a sensor 36. The sensor 36 relays the data to a processing device 38. The sensor 36 may or may not be in physical contact with the element 30. The processing device 38 processes the data in the same method as described above with reference to the continuous cure monitor.

Although exemplary embodiments have been shown and described, those skilled in the art will recognize that other embodiments fall within the spirit and scope of the invention. Accordingly, the invention is not limited to the disclosed embodiments, but rather is defined solely by the scope of the appended claims.

What is claimed is:

1. An apparatus for monitoring curing of a member including a resin, comprising:
   an energy source arranged to apply energy to the member; and
   a sensor which monitors curing by detecting the surface thermal energy of the member.

2. The apparatus of claim 1, wherein the energy source and the sensor are employed in a continuous manufacturing process.

3. The apparatus of claim 1, wherein the energy source and the sensor are employed in a batch manufacturing process.

4. The apparatus of claim 1, further comprising a processing device responsive to the sensor for processing the surface thermal energy of the member.

5. The apparatus of claim 1, further comprising an automatic controller for adjusting at least one curing parameter based on the surface thermal energy.

6. The apparatus of claim 5, wherein the curing parameter is selected from at least one of the duration and intensity of the energy applied to the member.

7. The apparatus of claim 6, wherein the energy source and the sensor are employed in a continuous manufacturing process, and wherein the duration of the energy applied to the member is adjusted by adjusting speed of the member in the manufacturing process.

8. The apparatus of claim 1, wherein the energy source is a heater.

9. The apparatus of claim 1, further comprising a plurality of energy sources arranged to apply energy to the member at different locations.

10. The apparatus of claim 1, further comprising a plurality of sensors which monitor curing by detecting the surface thermal energy of the member at different locations.

11. The apparatus of claim 1, wherein the sensor is non-destructive.

12. The apparatus of claim 1, wherein the sensor is non-intrusive.

13. The apparatus of claim 1, wherein the sensor does not contact the member.

14. An apparatus for verifying complete curing of a resin in a continuous manufacturing process, comprising:

a plurality of heaters arranged to apply energy to the resin;

a plurality of sensors which detect thermal surface energy of the resin without contact with the resin;

a processing device which processes the thermal surface energy from the sensors; and an automatic controller which adjusts at least one curing parameter in response to the processing device.

15. An apparatus for monitoring curing of a member including a resin, comprising:

means for applying energy to the member;

means for detecting thermal surface energy of the member;

means for processing the thermal surface energy of the member; and means for automatically controlling at least one curing parameter based on the surface thermal energy.

16. A method for monitoring curing of a member including a resin, comprising:

applying energy to the member;

detecting surface thermal energy of the member; and monitoring curing of the resin based upon the surface thermal energy.

17. The method of claim 16, wherein the monitoring is employed in a continuous manufacturing process.

18. The method of claim 16, wherein the monitoring is employed in a batch manufacturing process.

19. The method of claim 16, further comprising:

processing the surface thermal energy.

20. The method of claim 16, further comprising:

determining if the member has achieved a complete cure.

21. The method of claim 20, wherein a complete cure is achieved when the amount of energy being applied to the member is equal to an amount of energy being radiated from the member.

22. The method of claim 16, further comprising:

adjusting at least one curing parameter.

23. The method of claim 22, wherein at least one curing parameter is adjusted automatically in response to the surface thermal energy of the member.

24. The method of claim 22, wherein at least one curing parameter is adjusted manually in response to a cure profile generated from the surface thermal energy of the member.

25. The method of claim 22, wherein the curing parameter is selected from duration and intensity of the energy applied to the member.

26. The method of claim 16, wherein the energy applied to the member is heat.

27. A method of claim 16, wherein detection of the surface thermal energy does not destroy integrity of the member.

28. A method of claim 16, wherein detection of the surface thermal energy does not intrude into the member.

29. A method of claim 16, wherein detection of the surface thermal energy does not contact the member.

30. A method of verifying complete curing of a resin in a continuous manufacturing process, comprising:

applying heat to the resin;

monitoring surface thermal energy of the resin without contact with the resin;

processing the surface thermal energy of the resin to create a cure profile; and determining if the resin has reached a complete cure.

* * * * *